United States Patent [19]

Müller et al.

[11] 4,282,080

[45] Aug. 4, 1981

[54] ELECTROCHEMICAL SENSOR, PARTICULARLY FOR OXYGEN DETERMINATION IN COMBUSTION GASES

[75] Inventors: Klaus Müller, Tamm; Ernst Linder, Mühlacker; Helmut Mauer, Schwieberdingen; Karl-Hermann Friese, Leonberg; Franz Rieger, Aalen; Heinz Geier, Gerlingen, all of Fed. Rep. of Germany

[73] Assignee: Robert Bosch GmbH, Stuttgart, Fed. Rep. of Germany

[21] Appl. No.: 121,632

[22] Filed: Feb. 14, 1980

[30] Foreign Application Priority Data

Mar. 10, 1979 [DE] Fed. Rep. of Germany ....... 2909452

[51] Int. Cl.³ .............................................. G01N 27/58
[52] U.S. Cl. .................................................. 204/195 S
[58] Field of Search ............................ 204/1 S, 195 S

[56] References Cited

U.S. PATENT DOCUMENTS

| | | | |
|---|---|---|---|
| 3,691,023 | 9/1972 | Ruka et al. | 204/1 S |
| 3,719,564 | 3/1973 | Lilly et al. | 204/1 S |
| 4,107,019 | 8/1978 | Takao et al. | 204/195 S |
| 4,157,282 | 6/1979 | Riddel | 204/195 S |
| 4,157,948 | 6/1979 | Maurer | 204/195 S |

FOREIGN PATENT DOCUMENTS 2304464 8/1974 Fed. Rep. of Germany ....... 204/195 S
2711880 9/1978 Fed. Rep. of Germany ....... 204/195 S

*Primary Examiner*—G. L. Kaplan
*Attorney, Agent, or Firm*—Frishauf, Holtz, Goodman & Woodward

[57] ABSTRACT

To facilitate mass production and permit ready introduction of a substance which provides an oxygen partial pressure reference level, for example the oxygen in ambient air, an elongated plane flat plate-like solid electrolyte body is provided with electrodes thereon, and one of the electrodes is covered by a trough-like cover element to form the reference electrode, the space beneath the trough-like element and the electrode itself being available for the substance which may, but need not be, the oxygen of air, and may be a solid material providing a reference oxygen partial pressure level. The cover plate may, itself, be made of solid electrolyte material and may form a portion of another sensing element, so that a plurality of sensing elements can be superimposed in sandwich-like fashion. A heater element can be applied to a flat plate element of the assembly where desired. The sensors can operate in the potentiometric or polarographic mode.

13 Claims, 6 Drawing Figures

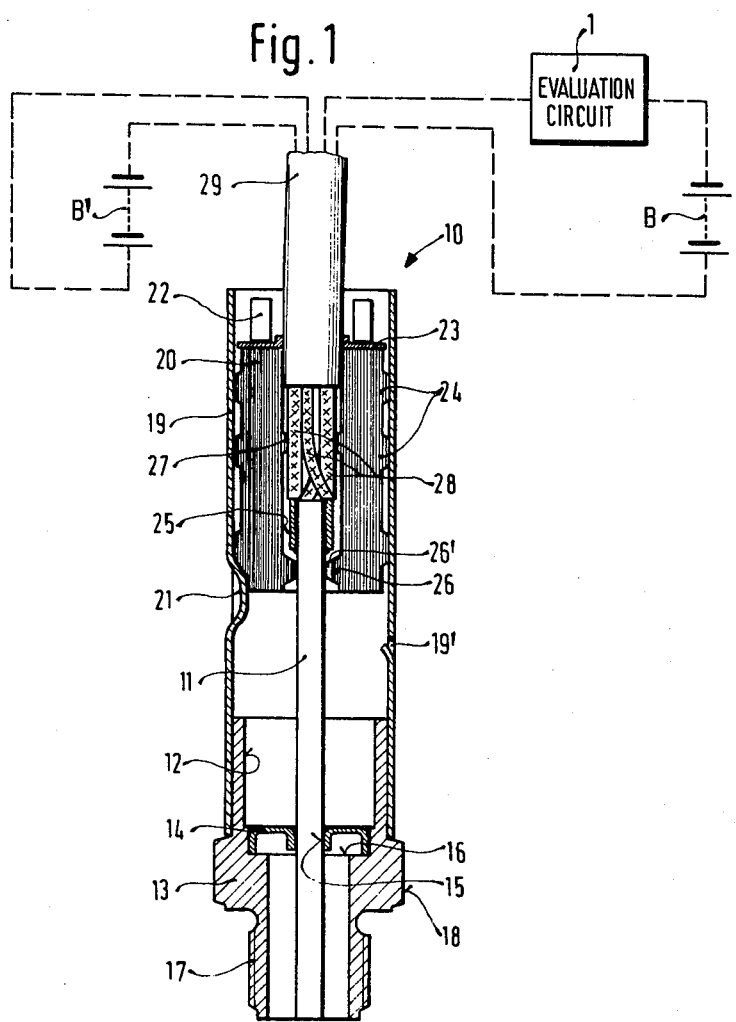

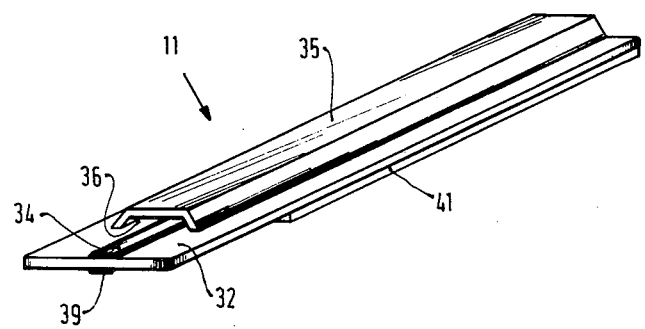
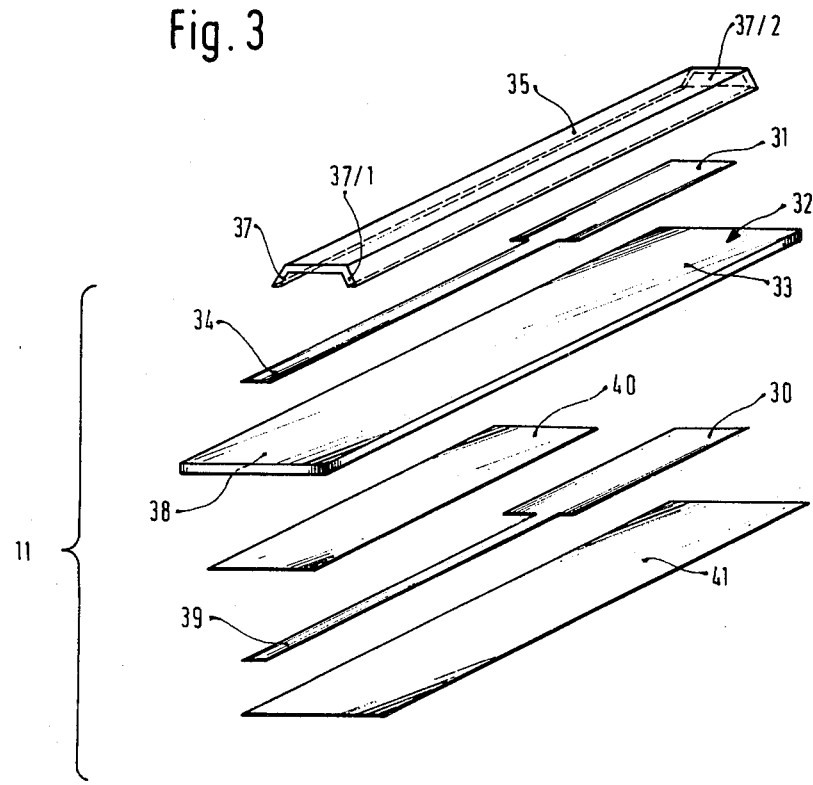

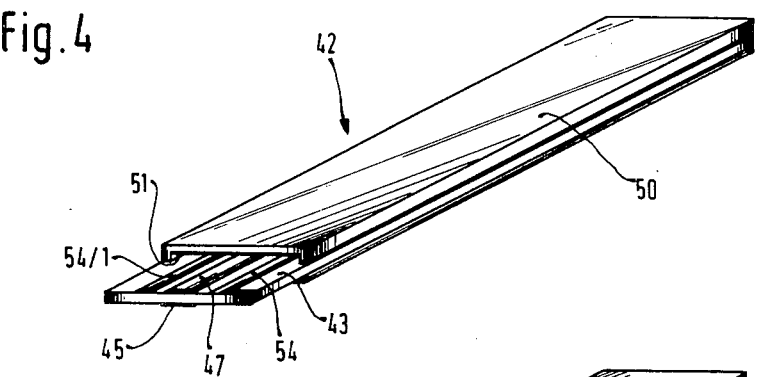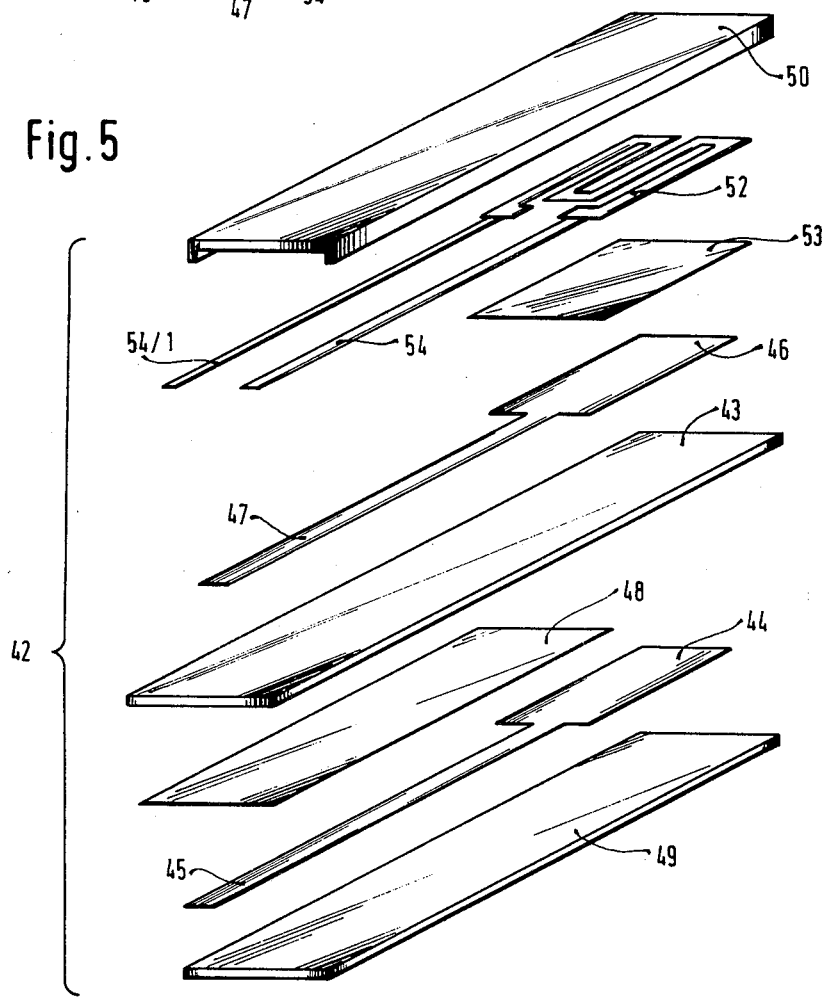

ELECTROCHEMICAL SENSOR, PARTICULARLY FOR OXYGEN DETERMINATION IN COMBUSTION GASES

CROSS REFERENCE TO RELATED PATENTS AND APPLICATIONS

U.S. Pat. No. 4,019,974, Weyl and Steinke
U.S. Pat. No. 3,978,006, Topp et al.
U.S. Pat. No. 4,021,326, Pollner et al.
U.S. Ser. No. 6,093, filed Jan. 24, 1979, CIP of Ser. No. 885,368, filed Mar. 13, 1978, now abandoned Dietz;
U.S. Ser. No. 121,600, filed Feb. 14, 1980, Müller et al.,
U.S. Ser. No. 121,599, filed Feb. 14, 1980, MAURER,
all assigned to the assignee of the present application.

The present invention relates to an electrochemical sensor, particularly to determine the oxygen content in combustion gases and especially in the exhaust gases from internal combustion engines, for example of the automotive type.

BACKGROUND AND PRIOR ART

Various types of sensors to determine the composition of exhaust gases from internal combustion engines have been proposed. One such sensor, for example, is described in U.S. Pat. No. 4,019,974, Weyl and Steinke, issued Apr. 26, 1977. This sensor has a solid electrolyte body which is made in form of a closed tube and in which electrodes and conductive tracks are formed. It is comparatively expensive to make such a sensor and to apply the respective electrodes, conductive tracks, and other layers thereon, as well as to make the electrical connections. The tubular element must be fitted into a longitudinal bore of a metal housing. The structure requires a comparatively large amount of materials and is labor-intensive. The response sensitivity and speed of such a sensor can still be improved. This type of sensor operates according to the potentiometric principle, that is, it functions as a true voltage-generating cell, providing an output potential when the exhaust gases and the reference gas have certain oxygen content relationships.

It is desirable to provide a sensor structure which can operate in accordance with the potentiometric principle but which, also, lends itself to use as a polarographic sensor, if suitably formed. A polarographic sensor is described, for example, in U.S. application Ser. No. 6,093, filed Jan. 24, 1979, Dietz, to which German Published Patent Disclosure Document DE-OS No. 27 11 880 corresponds. This sensor also is difficult to construct and it would be desirable to improve the sensor construction so that the sensor structure can be made at a lesser cost and with a higher degree of reproducibility, while providing a sensor having better response characteristics.

THE INVENTION

It is an object to provide an electrochemical sensor construction which is basically applicable to both a polarographic as well as to a potentiometric sensor, and which lends itself to mass production of the sensor at a lower cost, while providing a sensor which has better response speed and sensitivity.

Briefly, the solid electrolyte body is an essentially plane, flat plate; a trough-shaped cover element is applied over one face of the plate, which also has a reference electrode secured thereto. The trough-shaped element, by virtue of the recess formed by the rims thereof, leaves a clear space beneath the cover element and the plane, flat surface of the solid electrolyte body, on which the reference electrode is applied and defines a chamber therebeneath; this free space is available to receive a reference substance, for example oxygen derived from ambient air so that, upon application of a sensing electrode to the other plane surface, the sensor can function as a potentiometric sensor upon establishing communication to ambient air with the space beneath the trough-shaped cover element. A sensing element may be applied to the cover which, itself, may consist of an oxygen ion conductive solid electrolyte, and supplied with electrodes and conductive connection tracks. If it is desired to operate the sensor as a polarographic sensor, then it is only necessary to cover the sensing electrode with a material having a predetermined diffusion resistance to oxygen ion molecules, and connecting the electrodes to a suitable source of electric energy supply.

The sensor has the advantage over the sensors of U.S. Pat. No. 4,019,974, and of application Ser. No. 6,093, referred to above, that the particular structural relationship of the solid electrolyte body with the other elements thereof, and particularly with the trough-shaped cover which defines a hollow space above one of the electrodes, can be made inexpensively and is particularly suitable for mass production assembly. The sensor structure is also suitable to apply a plurality of such sensors on the same solid electrolyte body—which is made of comparatively expensive material, thus increasing the flexibility and output signals therefrom; further, it is simple to apply heating elements thereto so that the response sensitivity can be further increased.

DRAWINGS

FIG. 1 is a highly schematic longitudinal cross-sectional view through a sensor structure, to an enlarged scale, and operative as a potentiometric sensor to be used with a reference substance;

FIG. 2 is a perspective view, to a still more enlarged scale, of the sensor element operating on the potentiometric principle;

FIG. 3 is an exploded view of the potentiometric sensor element of FIG. 2, to an enlarged scale;

FIG. 4 is a perspective view of a polarographic sensor with a heater, to an enlarged scale;

FIG. 5 is an exploded view to an enlarged scale of the sensor of FIG. 4; and

Figure 6:
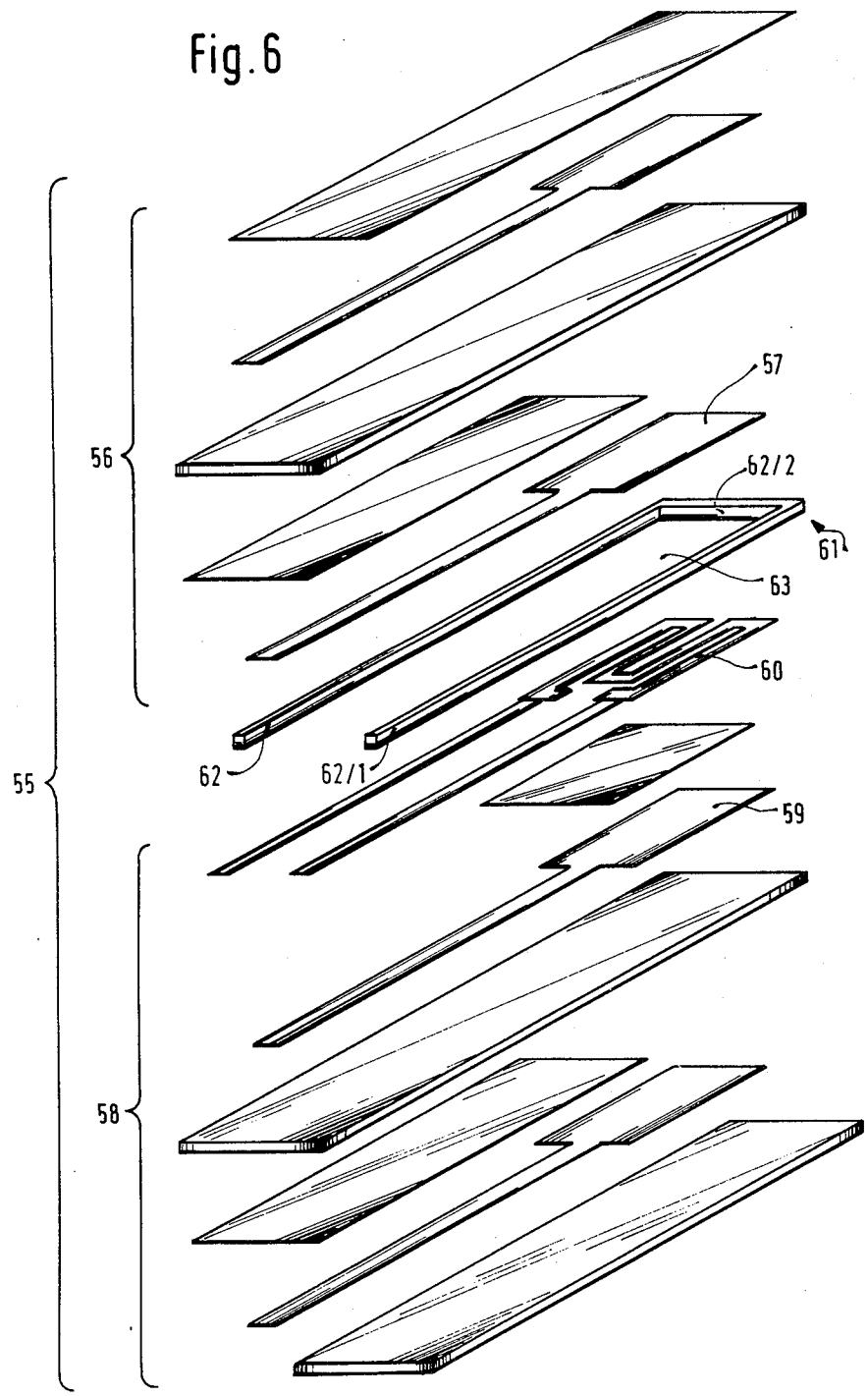
FIG. 6 is an exploded view of a sensor element combination, in which a heated polarographic sensor and a potentiometric sensor and constructed in accordance with the present invention are combined into a unit, to an enlarged scale.

The sensor 10 of FIG. 1 is used to determine the oxygen content of gases, especially gases resulting from a combustion process, particularly exhaust gases from internal combustion engines. It is suitable for use with engines of the automotive type, and especially for association with the exhaust system thereto. The sensor has a sensor element 11 which can operate either in accordance with potentiometric or polarographic measuring principle, as described in the referenced U.S. Pat. Nos. 3,978,006, Topp et al., and 4,021,326, Pollner et al., or in U.S. application Ser. No. 6,093, Dietz, filed Jan. 24, 1979, respectively. The sensor element 11 is an elongated, essentially rectangular plate which has a sensor portion adapted to be exposed to the combustion gases, a terminal portion at the other end for connection to connecting terminals, and an intermediate portion. The sensor element 11 is secured within the metal housing 13 and extends in a longitudinal bore or opening 12 thereof. It is retained in the metal housing by a holding element 14. Holding element 14 preferably is in disk form, and consists of a metal disk with a central opening 15, formed with a collar or flange bearing against the sensor element 11 and holding it in position. The sensor element 11 is sealed in the opening 15 by a solder, which may be a glass solder, hard solder, or the like, to be secured in gas-tight relation therein. The element 14 is formed at its outer circumference with a flange which is seated on an abutment 16 formed in the longitudinal bore of the housing and also sealed thereto. Thus, the disk 14 is sealed at both the outer and inner circumferences to the respective engaging elements, namely the metal housing 13 and the sensor element 11. The sealing material connecting the disk 14 with the metal housing 13 preferably also is a glass solder or glass seal or hard solder or weld connections, adhesives, or cements may also be used. Usually a single holding disk 14 in order to hold the sensor element in position is sufficient; in some cases, however, two or more holding elements similar to element 14 may be recommended. Although the element 14 could consist of ceramic rather than being made of metal, it is preferred to make it of metal. A metal disk is more elastic and can more readily accept change in temperature and thus will be more reliable in continued use. If a ceramic is used, connections between ceramic and metal portions, or ceramic parts among each other, preferably are connected by suitable metal-to-ceramic seals in which the respective ceramic portions are metallized at their surface before a solder connection is made.

The metal housing 13 is designed to be fitted into a pipe or conduit which carries the gases, the composition of which is to be measured. For example, housing 13 is adapted to be screwed into an exhaust pipe or the exhaust manifold of an internal combustion engine. It is formed with an outer thread 17 and a wrench engaging surface 18. The metal housing itself is axially short in order to save material, and is extended upwardly by a metal sleeve 19 over the measuring end portion of the element 11. Preferably, housing 13 and the sleeve 19 are welded together. An insulating bushing or plug 20 is positioned within the metal sleeve 19 and held in place by several inwardly pressed dimples 21. Strain relief tabs 22 additionally can be punched out of the metal sleeve and hold the plug 20 in position. A metallic abutment disk 23 is located between the plug 20 and the tension relief projections 22 in order to protect the plug 20 against mechanical stress. The insulating plug 20 which, in order to simplify assembly into the sleeve 19, is formed with externally projecting rings 24, has a central opening 25 extending therethrough formed with inwardly projecting sealing shoulders 26, 27. Sealing shoulder 26 additionally retains a sensor element 11 in position. Sealing shoulder 27 engages the electrical connections and connecting lines of a sensor connecting cable 29. The connection lines 28 are connected to an evaluation circuit 1 and, in certain cases, further, to a source of electrical energy, which may be a controlled voltage source B, as well known. None of these elements forms part of the present invention.

Sensor element 11 extends at its measuring end portion approximately flush with the end of the metal housing 13, or may be slightly recessed within the central opening thereof. Thus, it is not absolutely necessary to provide additional protective shields or the like to protect the sensor elements against particles in the measuring gas which might impinge thereon. The sensor element 11 is so connected to the electrical conductors 28 that the conductors 28 are galvanically isolated from the sensor housing 13. It is, of course, also possible to connect one of the lines to the housing and at the chassis or ground connection form one of the connecting lines to the battery and the evaluation circuit.

The sensor element 11 itself is illustrated in greater detail in FIGS. 2 and 3.

The sensor element 11 has an oxygen ion conductive solid electrolyte body 32, for example zirconium dioxide, in elongated, essentially rectangular plate-like form, to which a measuring electrode 30 is applied at one side and a reference electrode 31 at the other. The sensor operates in accordance with a well known oxygen concentration cell principle utilizing an oxygen ion conductive solid electrolyte body. The solid electrolyte body 32 is an elongated plane flat plate of about 5 mm width and of about 0.6 mm thickness.

The upwardly directed (FIGS. 2, 3) major plane surface 33 of the solid electrolyte body 32 has a layer-like porous reference electrode 31 applied thereto, positioned in the sensing portion of the plate 32. Any suitable and well known process may be used, such as application by printing, vapor deposition, or the like. The reference electrode 31 consists of an electron conductive material such as, for example, platinum, which has a thickness of, for example, 7 $\mu$m. A conductive track 34 which, preferably, also consists of platinum metal, connects the reference electrode longitudinally of the sensor element 11 to the terminal end portion thereof.

In accordance with the invention, the reference electrode 31 and the conductive track 34 are encapsulated by a gas-impervious cover 35 which is essentially trough-shaped, that is, is upwardly relieved and having a concave inner surface, so that a space or chamber 36 will remain between the cover 35 and the reference electrode 31. The space 36 has a cross section of about 2.5 mm width and height of about 0.5 mm. The cover 35 is formed with two side walls 37, 37/1 and a cross connecting end wall 37/2. The side walls and the end wall are securely attached to the major surface 33 of the solid electrolyte plate 32. The cover 35, preferably, is made of a ceramic material, for example zirconium dioxide and secured to the solid electrolyte plate 32 by sintering. A fourth end wall (not shown) which also closes off the space 36 at the terminal end portion of the solid electrolyte body 32 is needed only if a reference substance is located within the space 36 which is other than ambient air. If ambient air is utilized as the reference oxygen, the side wall at the left (FIG. 3) of the cover 35 can be left open. Other materials may be used, however, which have a predetermined oxygen partial pressure such as, for example, a mixture of metal and metal oxide, for example nickel/nickel oxide. If such materials are positioned in space 36, then an end wall similar to end wall 37/2 should be applied also at the other end of the cover 35. The cover 35, has a wall thickness of 0.5 mm and leaves the terminal end portion of the solid electrolyte body 32 uncovered so that the conductive track 34 unitary with the reference electrode 31 can be appropriately mechanically and electrically securely connected to the corresponding conductor 28 of the connecting cable 29. The reference electrode 31 may be protected by a porous protective layer made, for example, of magnesium spinel in order to protect the reference electrode 31 against attack by the measuring gas. Such a porous cover layer is necessary only in selected instances and, since not required, is not shown. The metal sleeve 19 is formed with air ingress openings 19' in order to permit access of ambient air to the space 36 so that the oxygen within ambient air can serve as reference substance with predetermined oxygen partial pressure within the sensor space 36. Additional openings or duct paths 26' can be formed within the holding shoulder or ring 26 to permit passage of air from the outside through suitable holes, slots, or other openings 19', of which only one is shown, to the interior of the sensor to form the reference substance.

The lower plane surface 38 (FIGS. 2, 3) has a measuring electrode 30 applied thereto, positioned opposite the reference electrode 31. The measuring electrode 30 is made of a material which catalyzes the setting of the gas equilibrium, for example made of porous platinum. Its construction and method of application may be similar to that of the reference electrode 31 and it is also formed with a conductive track 39 which extends to the terminal end portion of the solid electrolyte body 32. The conductive track 39 and/or the reference electrode conductive track 34 is insulated with respect to the solid electrolyte plate 32 by an electric insulating strip or layer 40 consisting, for example, of aluminum oxide, so that, in operation, the measuring signal is not subject to disturbances or attenuation due to stray or leakage currents between the conductive tracks 34, 39 passing through the solid electrolyte plate. The measuring electrode 30, and at least that portion of the track 39 exposed to the measuring gas, is protected against attack by the hot measuring gases by a protective layer 41 which, at least in the region of the measuring electrode 30, is porous. To permit connection of the conductive track 39 with a line or lead of the connecting lines 28, the protective layer 41 terminates short of the end portion at the terminal portion so that a solder or other connecting zone is left free. The protective layer or cover 41 may consist, for example, of magnesium spinel.

Embodiment of FIGS. 4 and 5: The sensor 42 which, similar to the sensor 11 of FIGS. 2 and 3, has a plate-like solid electrolyte body 43, has a measuring electrode 44 applied to one side thereof. Measuring electrode 44 is connected to a conductive path or track 45. The other side of the solid electrolyte 43 has a reference electrode 46 with a conductive track 47 applied thereto. This sensor operates according to polarographic measuring principle. The electrically insulating layer 48 separates signals passing through the conductive tracks 45, 47 from each other and from short circuit or stray or leakage currents through the plate 43. A porous cover layer 49 is applied to the sensing electrode 44, the cover layer 49 having a predetermined diffusion resistance to oxygen molecules within the gas to be analyzed. Simultaneously, they provide protection for the measuring electrode 44 against the hot exhaust gases. Cover layer 49 may consist, for example, of aluminum oxide having a thickness of about 0.5 mm. It preferably extends also over the conductive track 45 to form a protective layer therefor as well. The sensor element 42, like sensor element 11, has a gas-tight cover 50 which is applied to the side of the plate 43 carrying the electrode 46 and track 47 and forms, with respect to the reference electrode 46 and the track 47, a hollow space 51. In addition, a layer-like heating element 52 is positioned beneath the cover 50. It is isolated from the reference electrode 46 by a porous electrical insulating layer 53 made, for example, of aluminum oxide. The heater element 52 is of platinum metal and extends in meander or zig-zag configuration. The conductive track forming the heater element has a thickness of 10 μm and is extended by two conductive paths or tracks 54, 54/1 to the terminal end portion of the solid electrolyte plate 43. The conductive paths or tracks 54, 54/1 are parallel to the reference electrode track 47, but are laterally offset therefrom, extending along the edge portions of the solid electrolyte body 43. A protective layer can be applied on the heating element 52 and on the conductive paths 47, 54, 54/1—not shown—leaving, however, the terminal portions uncovered in order to permit establishment of an electrical connection thereto. The protective layer is gas-pervious at least in the region adjacent the windings of the heater element 52. It is required only under highly unfavorable operating conditions of the sensor.

The cover 35 of the sensor element 11 (FIGS. 2, 3) is a separately manufactured part which is connected with the solid electrolyte body after the solid electrolyte body has the electrodes 30, 31, conductive tracks 34, 39 and layers 40, 41 applied thereto. This method of application is also suitable for the sensor element 42. The assembly can be carried out differently, however, for example as follows: The cover 50 is applied to the solid electrolyte body 43 after the respective electrodes 44, 46, the insulating layer 53, the heater element 52 and the conductive tracks 54, 54/1 connected thereto and the outer cover layer 49 are assembled thereto to form a sensor subassembly. Thereafter, and using a void-forming material, for example carbon, the cover 50 is pressed together with the other elements on the body 43. Upon subsequent sintering, the carbon will be removed and leave the void or free space 51. Rather than using materials which form voids, a slider introduced between the heating element 52 and the cover 50 may be introduced during sintering, for subsequent removal.

The sensor element 42 may retain in the free space 51 a specific reference material providing a predetermined oxygen partial pressure; alternatively, the space may be left empty and ambient air or other gaseous material may be used to supply the reference material. If a substance other than ambient air is used, it can be enclosed within the space 51 and retained therein by forming a further side wall at the left side (FIG. 4) of the cover.

Embodiment of FIG. 6: The sensor element 55 is a combined sensor having a unit 56 which operates in accordance with a voltage cell, that is, on the potentiometric principle, and which is similar to the sensor element 11, but does not have the cover 35 (FIGS. 2, 3). Rather, it forms the cover of the overall combination. The sensor element 56 is so located within the arrangement that its reference electrode 57 faces downwardly, that is, reversed with respect to FIGS. 2–3. The second structural element of the combination 55 is a sensor element 58 which operates in accordance with the polarographic measuring principle. This unit approximately corresponds to the sensor element 42 of FIGS. 4, 5, but also does not have a cover corresponding to element 50 in FIGS. 4, 5. The sensor element unit 58 is so located in accordance with FIG. 6 that its reference electrode 59 and the heating element 60 face upwardly.

The third unit of the combination 55 is a U-shaped insulation frame 61 made, for example, of zirconium dioxide or other ceramic which is so positioned between the sensor elements 56, 58 that the two longitudinal legs 62, 62/1 and the U-shaped bottom or cross elements 62/2 commonly form with the sensor elements 56, 58 the free space 63, as described in connection with the sensor elements 11 and 42. The sensor element combination 55 can be constructed of two elements if at least one of the solid electrolytes plates is made with a frame-like rim projecting from the major plane thereof. The frame structure 61 can then be omitted as a separate element since its function is assumed by the projecting rim.

The combination 55 of FIG. 6 has a sensor element 56 operating according to potentiometric or voltage cell principle, and a sensor element 58 operating in accordance with the polarographic principle. Combination of two sensors, both operating in accordance with the potentiometric principle, or of two sensors, both operating in accordance with the polarographic principle, are possible. The combination 55 may use in the space 63 any suitable reference substance, such as a gaseous substance—typically ambient air—or another substance having a predetermined oxygen partial pressure, as previously explained. The combinations 55 may have a heater element 60 applied to each one of the sensor elements 56, 58.

To make the structure of FIG. 6, the various elements can first be made separately, assembled, and sintered together; or they can be assembled by using slider elements or slidable tool portions to take up the free space 63 during manufacture; alternatively, a substance which forms voids, when heated, such as carbon, may be introduced in the space 63 between the frame 61. One of the sensor elements 56 or 58 may be used to determine, for example, oxygen content of the measuring gas, and if one of those sensor elements is sufficient to obtain a suitable output signal, then the other sensor element can be used to determine other physical or chemical characteristics of the measuring gas, for example the second sensor may be a temperature-sensitive sensor to determine the temperature of the structure. The flat cover of the sensor element thus can carry different types of sensors, for example, rather than using the electrode 39 of sensor 58, a thermocouple or other temperature-sensing arrangement can be used, in which case the solid electrolyte plate supporting electrode 39 can be replaced by a suitable closing cover and support element for the temperature sensing electrodes.

The connections from the respective conductive tracks are not shown in detail, since they will be obvious; the heater conductors 54, 54/1 can be connected, for example, to a suitable source of electrical energy such as a battery B' (FIG. 1).

Various changes and modifications may be made, and features described in connection with any one of the embodiments may be used with any of the others, within the scope of the inventive concept.

We claim:

1. Electrochemical sensor, particularly for determination of oxygen content in combustion gases, especially from an internal combustion engine, having a metal housing (13) formed with a longitudinal opening therethrough;
an elongated plate-like sensing element (11) having a sensing portion at one end thereof adapted to be exposed to the gases, a terminal portion at the other end for connection to an external circuit, and an intermediate portion, said plate-like sensing element being secured and sealed in said housing at said intermediate portion, with the sensing portion thereof projecting from the intermediate portion and being exposed to the gases;
said sensing element (11) including
an oxygen ion conductive solid electrolyte body (32, 43) in form of an essentially plane flat plate;
a reference electrode (31, 46) applied to one major surface (33) thereof;
an electron conductive sensing electrode (30) applied to the other major surface thereof and located opposite the reference electrode, the reference electrode being exposed to a reference substance having a predetermined oxygen partial pressure to provide a reference level,
conductor means (39, 34) extending from said electrodes to the terminal portion,
and a trough-like cover element (35, 50) having a concave inner surface covering the reference electrode (31, 46), secured to said one major surface of the solid electrolyte body (32, 43) with the concave surface facing said one major surface of the reference electrode, defining a chamber (36, 51) therebeneath and providing for clearance between the reference electrode and the inner surface of the trough-like cover element,
said reference substance being located in said chamber.

2. Sensor according to claim 1, wherein the trough-like cover element (35, 50, 63) extends towards the terminal portion of the sensing element (11) and is open at the terminal portion to permit circulation of a reference gas into the hollow space (36, 51, 63) and forming said reference substance.

3. Sensor according to claim 2, wherein said reference gas comprises ambient air, the oxygen within the ambient air providing the reference substance of predetermined oxygen partial pressure.

4. Sensor according to claim 1, wherein the trough-like cover element (35) has unitary side walls (37, 37/1), and end wall (37/2) and a cover portion connecting said walls, said walls being secured to said one major surface of the solid electrolyte body.

5. Sensor according to claim 4, further including (FIG. 6) an additional sensor element (56) positioned on the cover element.

6. Sensor according to claim 5, wherein the cover element comprises an oxygen ion conductive solid electrolyte body, and further electrodes are applied to said cover element.

7. Sensor according to claim 6, wherein one of the sensor elements (56) operates as a potentiometric sensor in the form of an oxygen ion conductive cell, and the other sensor element (58) operates in a polarographic sensing mode, and the connection means are connected to a source (B) of electrical energy.

8. Sensor according to claim 6, wherein both sensor elements (56, 58) operate in the potentiometric sensing mode, said sensor element forming electrochemical voltage cells.

9. Sensor according to claim 6, wherein both sensor elements operate in the polarographic mode, and both sensor elements are connected to a source (B) of external electrical energy.

10. Sensor according to claim 1, wherein (FIG. 6) said trough-like cover element (61) comprises a frame element (61) having side walls (62, 62/1) and an end wall secured to said one major surface (33) of the solid electrolyte body.

11. Sensor according to claim 1, wherein, to provide a potentiometric sensor, the sensing electrode (30) is porous and comprises a material capable of catalyzing the gas equilibrium;

and a porous protective layer (41) is applied over said sensing electrode.

12. Sensor according to claim 1, wherein (FIGS. 4, 5), to form a polarographic sensor, a cover layer (49) is provided covering the sensing electrode (44), said cover layer being characterized by having a predetermined diffusion resistance to the passage of oxygen molecules;

and connection means (28, 29) are provided to connect an electrical voltage (B) to the conductor means (45, 47).

13. Sensor according to claim 1, further including a heater element (52, 60) on the sensing element (11).

* * * * *